United States Patent
Thomson

(10) Patent No.: US 7,226,426 B2
(45) Date of Patent: Jun. 5, 2007

(54) APPARATUS AND METHOD FOR THE DETECTION AND QUANTIFICATION OF JOINT AND TISSUE INFLAMMATION

(76) Inventor: Paul E. Thomson, 5420 Haft Rd., Cincinnati, Hamilton County, OH (US) 45247-7422

( * ) Notice: Subject to any disclaimer, the term of this patent is extended or adjusted under 35 U.S.C. 154(b) by 558 days.

(21) Appl. No.: 10/205,410

(22) Filed: Jul. 25, 2002

(65) Prior Publication Data

US 2004/0019303 A1    Jan. 29, 2004

(51) Int. Cl.
A61B 5/117    (2006.01)
A61B 5/103    (2006.01)

(52) U.S. Cl. .................................................. 600/595
(58) Field of Classification Search ............... 600/595, 600/430, 549, 555, 401, 473, 590; 356/419; 374/122; 378/3; 702/19, 20; 435/6, 7.32; 318/518.11, 568.12; 180/8.1; 33/124; 382/240, 382/233, 284
See application file for complete search history.

(56) References Cited

U.S. PATENT DOCUMENTS

| | | | |
|---|---|---|---|
| 4,275,741 A * | 6/1981 | Edrich ........................ 600/430 |
| 4,445,516 A * | 5/1984 | Wollnik et al. .............. 600/549 |
| 4,530,367 A * | 7/1985 | Desjardins et al. ......... 600/590 |
| 5,311,109 A * | 5/1994 | Ozawa ................... 318/568.11 |
| 5,325,449 A * | 6/1994 | Burt et al. ................... 382/240 |
| 5,941,833 A * | 8/1999 | Lipman ...................... 600/555 |
| 6,057,925 A * | 5/2000 | Anthon ....................... 356/419 |
| 2002/0087274 A1* | 7/2002 | Alexander et al. ............ 702/19 |
| 2004/0019269 A1* | 1/2004 | Schaefer et al. ............ 600/407 |

* cited by examiner

*Primary Examiner*—Max Hindenburg
*Assistant Examiner*—Brian Szmal
(74) *Attorney, Agent, or Firm*—Mark F. Smith; Smith Brandenburg Ltd

(57) ABSTRACT

The apparatus and method for the detection and quantification of joint and tissue inflammation (100) of the present invention comprises a sensing component (102) for obtaining and collecting data indicative of the surface or dimensions of the joint or tissue. The sensing component (102) comprises various components for obtaining measurements of the cardinal signs of inflammation. Preferably the sensing component (102) includes a device for detecting swelling (104), a color analyzing device (108), a temperature measuring device (110), a pain or tenderness detection device (112), an archival and retrieval device (114), and a display device (116). In operation a patient is placed in position for examination of the joint or tissue area measurements are taken of one or more of the cardinal signs of inflammation at the joint or tissue area, the measurements are automatically stored in a archival storage and retrieval device (114), and from the measurements an inflammation score is derived which can be compared against a baseline.

32 Claims, 7 Drawing Sheets

APPARATUS AND METHOD FOR THE DETECTION AND QUANTIFICATION OF JOINT AND TISSUE INFLAMMATION

TECHNICAL FIELD

The subject invention relates to medical method and apparatus and more particularly to apparatus and method for the detection and quantification of joint and tissue inflammation.

BACKGROUND OF THE INVENTION

Most people by age 50 develop some degree of arthritis. Usually, this takes the form of degenerative joint disease, or osteoarthritis that eventually afflicts nearly everyone by the time they are 65 years old. Another form of arthritis, rheumatoid arthritis, affects approximately 1% of the population with a prevalence that approaches 2% of males and 5% of females by age 65. When lupus, gout, infectious processes, metabolic processes, toxins, cancers, and the more than 100 other types of arthritis are added to these numbers, nearly everyone, if they live long enough, will suffer joint pain and arthritis. The ultimate prevalence of joint diseases is further increased by fractures, athletic injuries, neuromuscular disorders, and congenital deformities.

Common to all of the various forms of joint diseases is the presence of inflammation. All forms of inflammation, from any cause, are characterized by five cardinal signs or manifestations comprising redness, swelling, heat, pain, and the loss of function of the involved tissue. The presence of inflammation in the involved joint or tissue indicates the presence of injury or disease, while the amount of inflammation in the injured, deformed, or arthritic joint or tissue is directly proportional to the amount of damage or disease in that joint and is inversely proportional to the degree of healing in the same joint. Accordingly, the physician or surgeon treating such musculoskeletal problems is constantly trying to detect any inflammation, and, if present, to assess the degree of this inflammation in order to determine whether disease or injury is occurring, how much disease or damage is present, and whether the problem is progressing or healing.

Various methods and equipment have been developed for assessing the presence or absence of inflammation in joints and other tissues. Such methods and equipment include performing a physical examination of the involved tissue; blood tests, such as erythrocyte sedimentation rate or C-reactive protein level; radiographic tests; such as plain X-rays or magnetic resonance imaging (MRI); and research procedures, such as thermography.

In performing a physical examination, the physician begins the method of assessing the presence or absence of inflammation by asking such questions as which joints or tissue areas are causing pain, how much pain is present and how often is the pain present. The physician will then perform a physical examination to determine if there is any redness, warmth, swelling, or stiffness in these areas, and to see if the patient is experiencing any limitation or loss of function. This method of questioning and physical examination of the patient, however, does not reliably establish the presence of inflammation. For example redness over an area of pain could he a result of an overlying skin rash rather than inflammation or stiffness may be a result of a nearby muscle spasm as opposed to inflammation. Further, this method results in an assessment that is only crudely and inconsistently quantifiable. For example, the physician might ask, "If zero equals no pain and your pain level was a 10 out of 10 when you were first treated, at what level is your pain currently?" Such clinometric scales are generally inconsistent and results will vary depending, among other factors, on the manner in which the questions were asked, the physician asking the questions and the day and time the patient was questioned. Accordingly, such assessments are highly subjective and ultimately have no definite correlation with the actual degree of inflammation.

In addition to determining the presence of inflammation, the physical examination may also provides some indication of the presence and degree of inflammation. The physician or surgeon, for example, may gently squeeze or palpate the involved joint or tissue to detect swelling, warmth, or tenderness. Even if the physician detects some amount of joint or tissue swelling by palpation, there is no precise and reproducible way of determining whether the swelling represents newly inflamed tissue or just residual thickened and scarred tissue from previous, now quiescent inflammation. Detection of skin warmth is useful but cannot be quantified by simple palpation. The determination of tenderness is also useful but it only inconsistently correlates with actual inflammation. For example, the joint or tissue could be tender secondary to conditions that are not related to inflammation, such as poor circulation, diabetic-related or other causes of local nerve damage, foreign bodies, and other causes. The degree of tenderness is often assessed using a clinometric scale and has the same drawbacks as previous mentioned. The range of motion of a joint or muscle represents that tissue's functional state. Typically, the method of measuring the range of motion of a joint or muscle involves holding a plastic protractor next to the joint while the patient tries to move the joint or muscle in question. Unfortunately, problems of accuracy and reproducibility arise due to placement and stability of the protractor. It has been found that results of testing will vary even between tests performed by the same examiner on the same patient.

The method of performing blood tests to assess the presence and degree of inflammation typically involves testing of erythrocyte sedimentation rate or C-reactive protein levels. Unfortunately, such tests are nonspecific and indicate changes taking place throughout the patient's body rather than to inflammatory changes taking place in localized areas, such as a knee or finger. Further, the results of the blood tests are uniformly subject to a wide variety of physical conditions and ailments that are not related to inflammation. For example, the blood count in a patient having significant arthritis or other forms of inflammatory disease may show elevations of the white blood cells or of other blood cells called "platelets." However, the White cell count can be elevated due to many conditions such as leukemia, allergies, drug reactions, and numerous illnesses that have little or no relationship with inflammation. Similarly, the platelet count may be increased by noninflammatory conditions such as an iron deficiency or cancer. In addition, in many inflammatory conditions such as rheumatoid arthritis, such cell counts typically show no elevation.

In the performance of another type of blood test commonly employed to detect inflammation, the erythrocyte sedimentation rate (ESR), the patient's anticoagulated blood sample is placed in a vertical glass or plastic capillary tube. After sitting for one hour, the height of the column of red blood cells that have settled to the bottom of the tube is measured. In general, the taller the column of red cells, the more inflammation exists in the patient's body. Unfortunately, this method has numerous problems. Similarly to the white blood cell and platelet tests mentioned above, the ESR may not show any elevation, eaten in the presence of clearly clinically detectable inflammation. This lack of elevation, or in some cases elevated levels not caused by inflammation, may be due to various conditions including anemia, sickled blood cells, bone marrow cancers, and diabetic kidney disease. Further, as with blood count tests, such methods only indicate the possibility of inflammation and reflect a systemic rather than a local situation.

Another blood test used in detecting inflammation involves the measurement of a patient's C-reactive protein level (CRP). Like the other blood tests used for detecting inflammation, CRP suffers from the lack of sensitivity, lack of specificity and numerous confounding factors.

As a result of the numerous difficulties associated with the various methods of assessing inflammation using blood tests and since these methods do not include measurement of the five above-mentioned markers of inflammation, such methods are indirect at best and only useful in obtaining adjuncts for detecting and quantifying inflammation.

Methods for detecting inflammation using plain radiographs, such as plain X-rays, have proved to be inadequate It has been found that if a patient has swelling capable of being shown in a X-ray, the swelling level would also be clinically evident on physical examination thereby rendering a X-ray unnecessary. In addition, any shadowy outline of a soft tissue bulge around a bone or joint indicating possible inflammation would be extremely nonspecific and may be produced by conditions that are unrelated to inflammation, such as obesity.

Methods using computerized tomography (CT) scans and magnetic resonance imaging (MRI) scans are performed occasionally to observe swelling in various tissues. Such methods, however, are relatively expensive, may be insensitive to very mild degrees of inflammation, and generally do not detect forms of inflammation that involve only minimal or no swelling. Additionally, the CT scan uses ionizing radiation. Further, an MRI cannot be used for individuals having pacemakers or metallic implants located near the subject area. Another problem with using CT and MRI scans is the difficulty of interpreting the results of the scans making them unsuitable for routine outpatient testing in a typical medical office or clinic.

Methods of detecting inflammation using thermography or infrared photography have been used to try to detect inflammation. Unfortunately, however, thermography is relatively insensitive to mild degrees of inflammation, it cannot detect any of the signs of inflammation except warmth, it is difficult to reproduce due to changes in regional blood flow, for example caused by emotional states, and it is relatively expensive and technically difficult, requiring the patient to be unclothed and placed in a climate-controlled room where ambient temperature and humidity are assiduously constant and stabilized.

Accordingly, a need exists for a relatively inexpensive, reliable, reproducible, easy to use or perform, noninvasive method and apparatus for the detection and quantification of joint and tissue inflammation that may be used in medical offices, clinics, sports and training facilities, and the like.

DISCLOSURE OF THE INVENTION

The present invention is directed to an apparatus and a method for the detection and quantification of joint and tissue inflammation comprising a sensing component for obtaining data indicative of the surface of a patient's skin or other tissue, a color analyzing device for analyzing the color of the patient's skin or other tissue, and a temperature measuring device for measuring the temperature of the patient's skin or other tissue.

In a preferred embodiment of the invention, the apparatus and the method for the detection and quantification of joint and tissue inflammation includes a device for determining the amount of loss of function of the joint, selected from a group of spatial orienting and localizing detectors.

In a preferred embodiment of the invention, the apparatus and the method for the detection and quantification of joint and tissue inflammation includes a device for measuring the pain threshold and tolerance of the joint or tissue, selected from the group of pain detecting devices.

In another preferred embodiment of the invention, the apparatus and the method for the detection and quantification of joint and tissue inflammation includes a sensing component which operates to detect swelling via generating measurements of the surface or three-dimensional or cross-sectional or complete spatial models or images of the joint or tissue area.

In another preferred embodiment of the invention, the apparatus and the method for the detection and quantification of joint and tissue inflammation includes a color analyzing device for analyzing the color of the subject joint or tissue comprising a light- or gloss-sensitive device, selected from a group of colorimeters, spectrophotometers, or glossmeters.

In another preferred embodiment of the invention, the apparatus and the method for the detection and quantification of joint and tissue inflammation includes a temperature measuring device for measuring the temperature of the joint or tissue and is a mechanical contact, optical, laser-based, thermistor type, thermometer, thermographic type, infrared-based, or surface electrical conductance-resistance based temperature measuring device.

Another preferred embodiment of the invention is a method of detecting and quantifying joint and tissue inflammation.

Another preferred embodiment of the invention is a method of detecting and quantifying joint and tissue inflammation comprising the step of using the apparatus of the subject invention.

A primary object of thus invention, therefore, is to provide an apparatus and a method for the detection and quantification of joint and tissue inflammation.

Another primary object of this invention is to provide a relatively inexpensive apparatus and method for the detection and quantification of joint and tissue inflammation Another primary object of this invention is to provide a relatively reliable apparatus and method for the detection and quantification of joint and tissue inflammation.

Another primary object of this invention is to provide an apparatus and a method that produces reproducible results for the detection and quantification of joint and tissue inflammation.

Another primary object of this invention is to provide a relatively easy to use apparatus and a method for the detection and quantification of joint and tissue inflammation.

Another primary object of this invention is to provide a safe and a noninvasive apparatus and method for the detection and quantification of joint and tissue inflammation.

Another primary object of this invention is to provide a apparatus and a method for the detection and quantification of joint and tissue inflammation that may be used and performed in medical offices, clinics, sports and training facilities, and the like.

Another primary object of this invention, therefore, is to provide a method that uses an apparatus for the detection and quantification of joint and tissue inflammation.

These and other objects and advantages of the invention will be apparent from the following description and the accompanying drawings.

BRIEF DESCRIPTION OF THE DRAWINGS

The details of the invention will be described in connection with the accompanying drawings, in which.

BEST MODE FOR CARRYING OUT THE INVENTION

Figure 1:
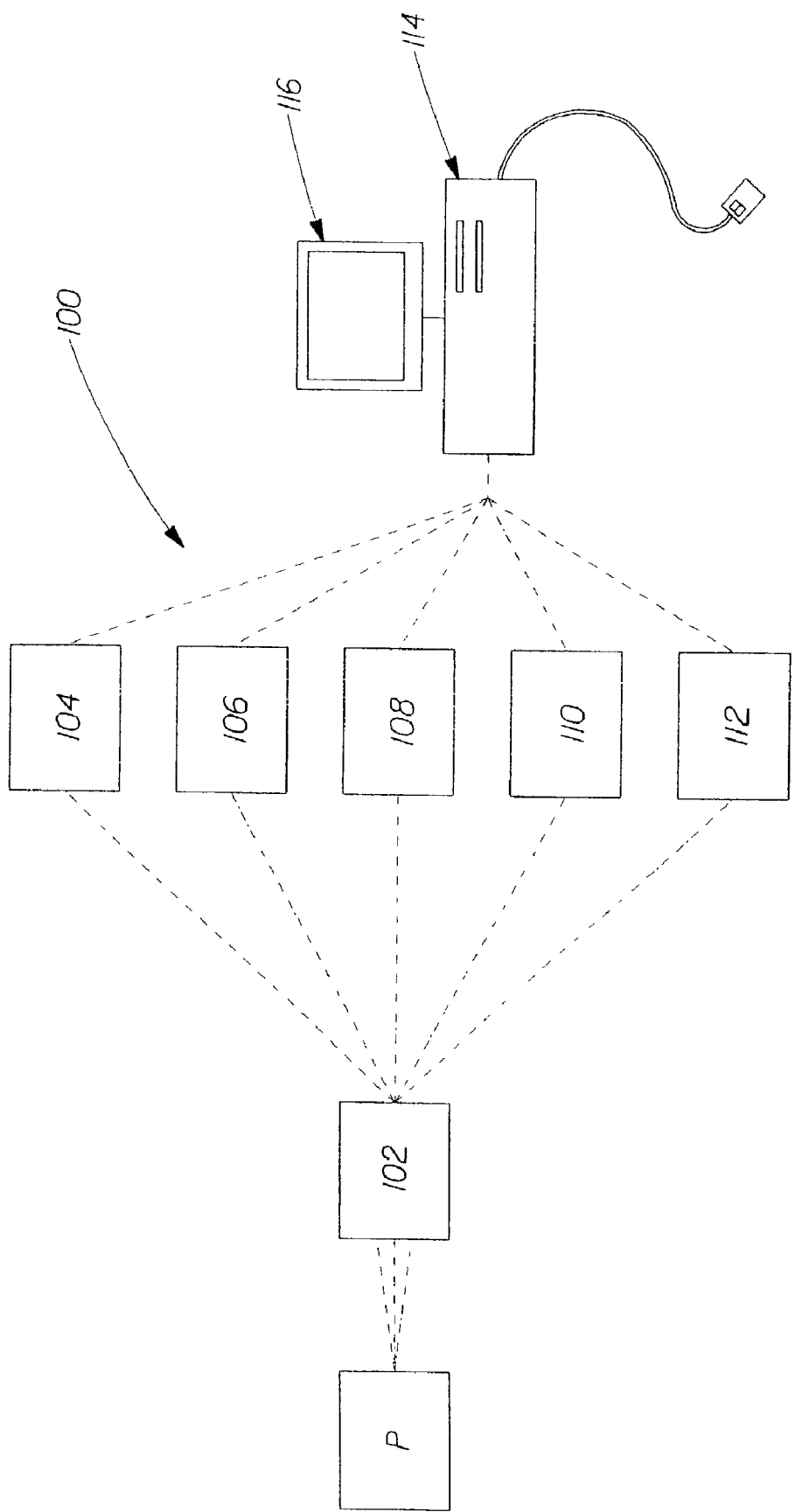
FIG. 1 is a schematic view of the apparatus for the detection and quantification of joint and tissue inflammation of the present invention.
Figure 2:
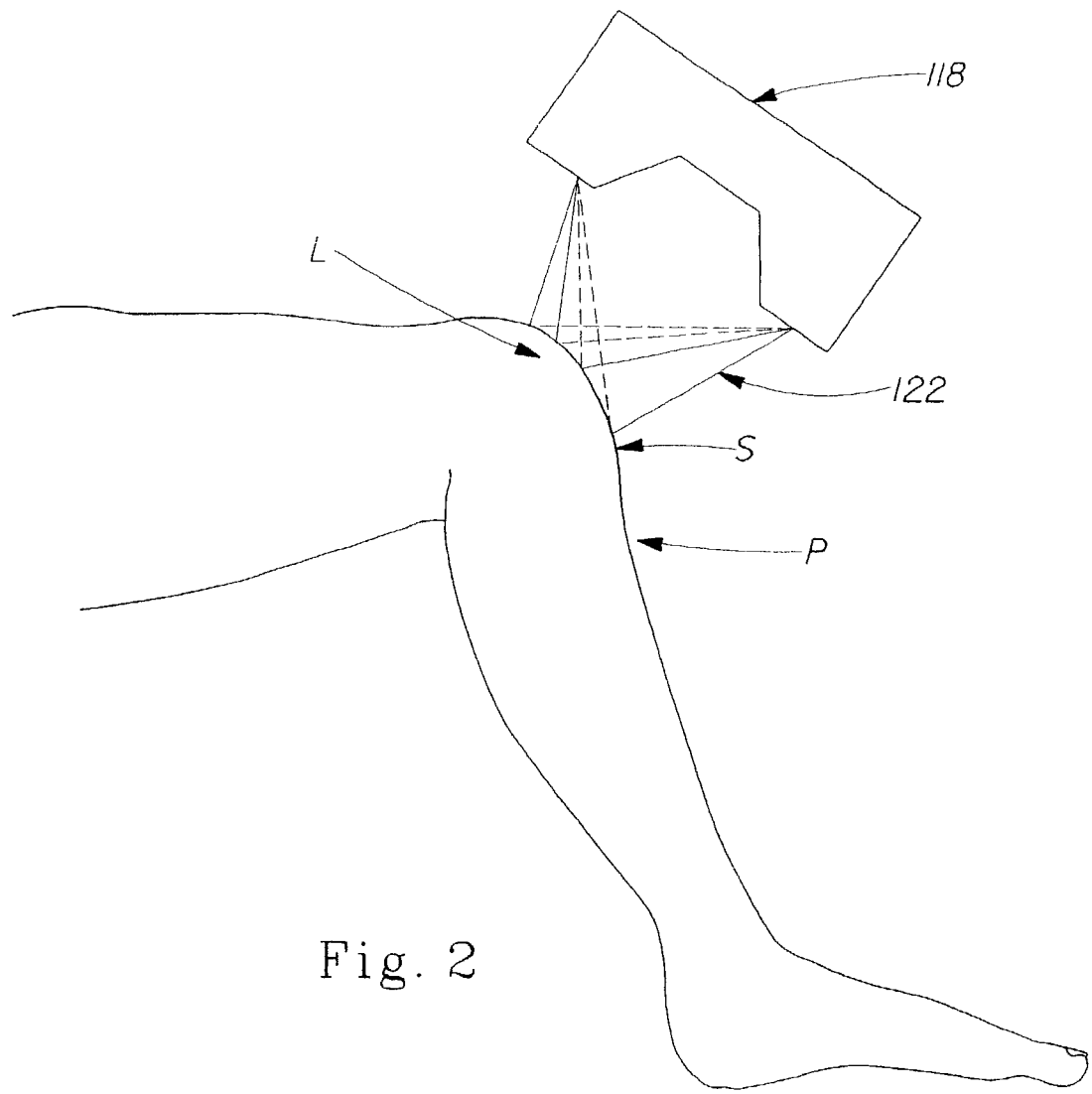
FIG. 2 is a schematic view of the surface scanning element of the sensing component of the apparatus for the detection and quantification of the subject joint or tissue of FIG. 1.

Referring to FIGS. 1 and 2, a non-human observer or non-clinician apparatus for the detection and quantification of joint and tissue inflammation, generally designated 100, is shown comprising a sensing component 102 for obtaining and collecting data indicative of the surface at the location L of the joint or tissue of a patient P. Preferably, the sensing component 102 comprises various components for assessing inflammation such as a device for detecting swelling 104, such as an optical imaging system, by providing dimensional measurement of the location L of the joint or tissue of the patient P being examined for inflammation, a range-of-motion device 106 for determining the patient's range of motion of the joint being examined, a color analyzing device 108 for analyzing color of the patient's skin at the location L of the joint or tissue, a temperature measuring device 110 for measuring the temperature of the skin S of the patient P at the location L of the joint or tissue, a pain detection device 112 for determining the threshold and tolerance of pain, an archival storage and retrieval device 114, such as a computer, for storing data being collected and for correlating and analyzing, and a display device 116 for viewing the analyzed data.

Referring to FIG. 2, a patient P being tested for joint and tissue inflammation is shown positioned such that the location L of the tissue or joint to be examined is appropriately positioned for measurement by the apparatus 100 of the present invention. The sensing component 102 includes a surface scanning element 118 having a digitizing scanner which is coupled for use with the device for detecting swelling 104 for dimensional measurement of the location L of the tissue or joint being examined for inflammation. Preferably, the surface scanning element 118 may comprise a flat bed scanner for providing two-dimensional images and measurement data of the location being examined, or multiple scanners, such as are used currently in the manufacture of high precision casting and machine components, for example, suitably oriented for providing three-dimensional images and measurement data of the area being examined. The device for detecting swelling 104 may also comprise various thermography devices, such as infrared imaging systems used for security identification, infrared inspection of electrical and mechanical components, or medical imaging. The device for detecting swelling 104 may also comprise high-resolution ultrasound or magnetic resonance systems, such as used in medical imaging.

Referring to FIGS. 1 and 2, an example of the preferred embodiment of the invention is shown whereby the device for detecting swelling 104 is a conventional video-based digitizing scanning system which is coupled to the surface scanning element 118 of the sensing component 102. The surface scanning element 118 operates to collect data and transfer the data to the device for detecting swelling 104, such as by the use of an analog to a digital converter (not shown), which is coupled to the archival storage and retrieval device 114 that operates to store and analyze the collected data to generate measurements, and preferably a mathematical model or image indicative of the surface and cross-sectional dimensions of the joint or tissue at the location L. The specific measurements and the mathematical model or image, if any, can be fed to the display device 116 for viewing.

In another preferred embodiment of the invention, the device for detecting swelling 104 is a conventional laser-based digitizing scanning system which is coupled to the surface scanning element 118 of the sensing component 102. The device 104 includes means for moving a light beam 122, such as a laser beam emitted from the surface scanning element 118 across the surface area of the location L being investigated. The surface scanning element 118 collects data and transfers the data to the device for detecting swelling 104 which is coupled to the archival storage and retrieval device 114 that operates to store the collected data and to analyze the pattern of reflections and the characteristics of the beam spot pattern of reflections from the scanned location L to generate a model or image indicative of the surface and cross-sectional dimensions of the Joint or tissue at the location L. The archival storage and retrieval device 114 then feeds the generated model or image, if any, and pertinent measurements to the display device 116 for viewing.

Figure 3:
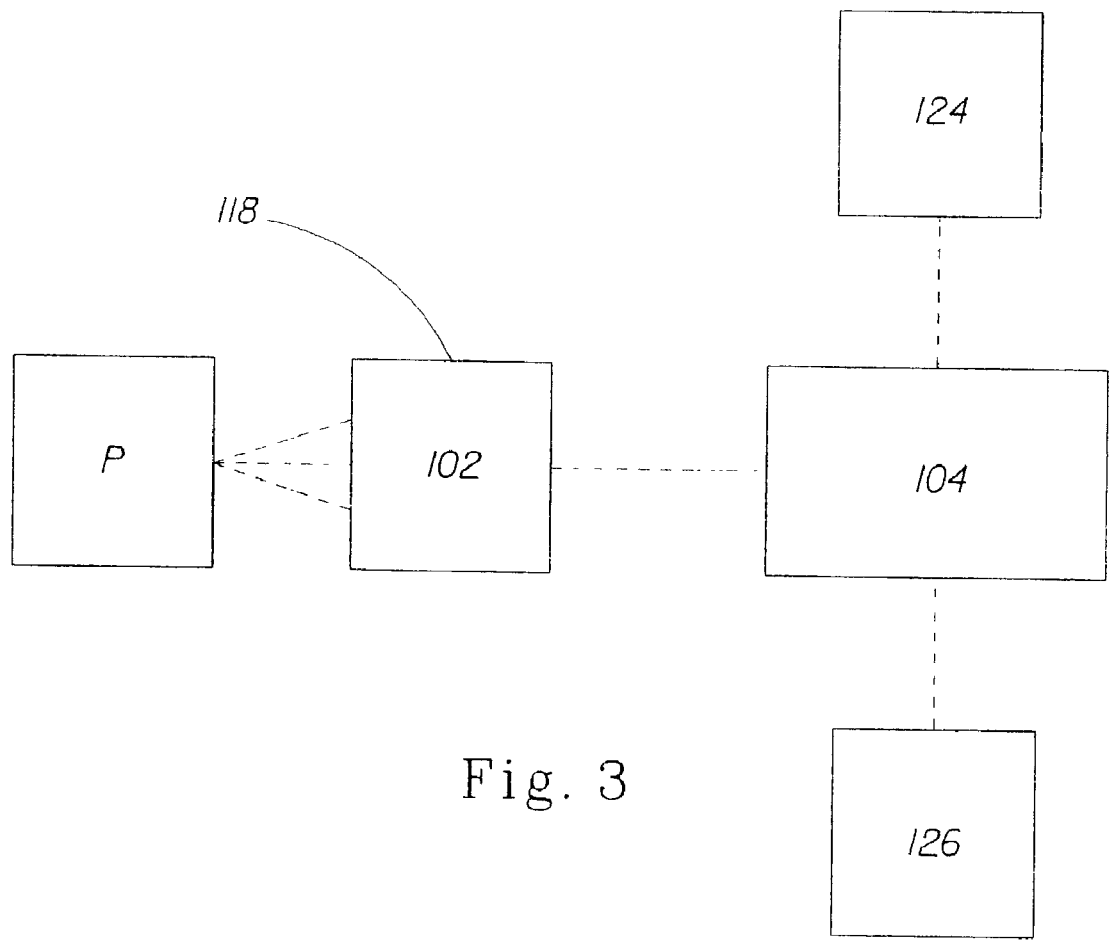
FIG. 3 is a schematic view of the sensing component of the apparatus for the detection and quantification of inflammation of FIG. 1, the sensing component having a distance or spatial measuring device or imaging device to measure the distance between the surface scanning element and the spatial or dimensional characteristics or image of the location being scanned of the subject joint and tissue of FIG. 1.

In another preferred embodiment of the present invention, the device for detecting swelling 104 is a conventional position tracking based scanning system which is coupled to the sensing component 102 having a hand-held, free-motion surface scanning element 118. Preferably, the surface scanning element 118 is manually moved about the location L to be scanned by an operator. Referring to FIG. 3, the imaging system 104 is shown having a distance measuring device 124 to measure the distance between the surface scanning element 118 and the surface at the location L being scanned and a position tracking device 126 to detect the position and orientation of the surface scanning element 118 within a position reference field. In operation, the device for detecting swelling 104 tracks the location of the surface scanning element 118 and is conventionally coupled to the archival storage and retrieval device 114 which receives location data from the device 104 and correlates and generates the cross-sectional dimensions, and preferably an image, of the scanned joint or tissue at the location L. The archival storage and retrieval device 114 then feeds the pertinent measurements and the generated image, if any, to the display device 116 for viewing.

In another preferred embodiment of the present invention, the device for detecting swelling 104 is a conventional position tracking based scanning system which is coupled to the sensing component 102 having a free-motion digitized surface scanning element 118. The position tracking system 126 detects the position of the surface scanning element 118 relative to a position reference magnetic field generated by a transmitter (not shown). In operation, the tissue or joint at the location L is measured by pressing the surface scanning element 118 against the skin S of the patient P and moving the surface scanning element 118 over the surface of the joint or tissue to be scanned. The position tracking system 126 tracks the position and orientation of the surface scanning element 118 as it moves over the location L and is coupled to the archival storage and retrieval device 114 which receives and correlates data and generates the cross-sectional dimensions, and preferably an image, of the joint or tissue at the scanned location L. The archival storage and retrieval device 114 then feeds the pertinent measurements and generated model or image, if any, to the display device 116 for viewing.

Figure 4:
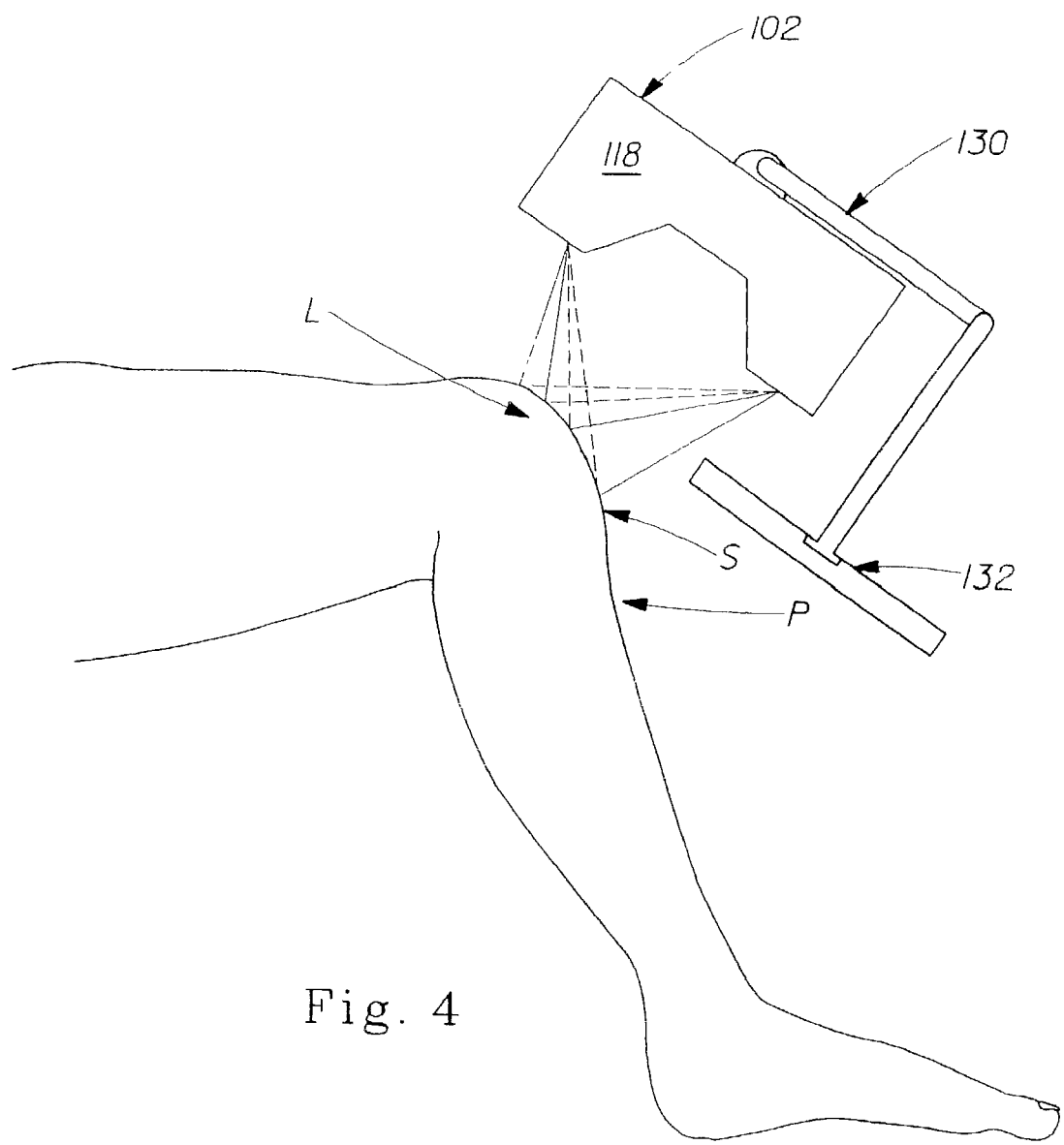
FIG. 4 is a schematic view of the sensor of the sensing component of the apparatus for the detection and quantification of inflammation of FIG. 1 showing a support stricture and guide track for supporting and directing the motion of the sensor unit.

Another preferred embodiment of the present invention, as shown in FIGS. 1 and 4, the device for detecting swelling 104 is a conventional position based tracking system and is coupled to the sensing component 102 having a non-contact, restricted motion surface scanning element 118. The device for detecting swelling 104 includes a support structure 130 for supporting the sensing component 102 and a guide track 132 for directing the motion of the sensing component 102 A conventional brace (not shown) may be provided to hold the limb or other anatomic feature of the patient P being scanned in place during scanning. Alternatively, the sensing component 102 may also be attached to a mechanical arm (not shown) for directing its motion over the area to be scanned. In a preferred embodiment of the invention, the distance measuring device 124 (FIG. 3) is a non-contact probe, such as a laser distance measuring device, that measures the displacement between the surface scanning element 118 and the skin S of the patient P at the location L being scanned. The position of the surface scanning element 118 is directed by a position tracking system 126 (FIG. 3) bed denoting the position of the surface scanning element 118 on the guide track 132 or the mechanical arm (not shown). In operation, the tissue or joint of the patient P is secured in place and the surface scanning element 118 is moved along the guide track 132 to scan the tissue or joint. The device for detecting swelling 104 tracks the position of the surface scanning element 118 and is conventionally coupled to the archival storage and retrieval device 114 which analyzes the scanned data and the position of the surface scanning element 118 and generates an image and cross-sectional dimensions of the tissue or joint at the scanned location L which is fed to the display device 116 for viewing.

Another preferred embodiment of the present invention, as shown in FIGS. 1, 2, 3, and 4, the device for detecting swelling 104 is a high-resolution ultrasound device and is coupled to the sensing component 102 heaving an ultrasound emitter and receiver scanning element 118. The ultrasound emitter and receiver scanning element 118 may be a hand-held, free-motion surface scanning device (FIG. 2) or a restricted-motion scanning element utilizing a support structure 130 and a guide track 132 (FIG. 4). A conventional brace (not shown) may be used to hold the limb or other anatomic feature of the patient P being scanned during the scanning operation. A position tracking device 126 may be attached to the device for detecting swelling 104 (FIG. 3) to determine the position and orientation of the ultrasound probe 118 within a position reference field. In operation, ultrasonic beams from the scanning element 118 are emitted through and then reflected back from the tissue of the patient P at the location L. The nature of, degree of, and the rapidity of the reflected ultrasound signal detected by the receiver sensor of the surface scanning element 118 are transmitted to the device for detecting swelling 104 which is coupled to the archival storage and retrieval device 114. The archival storage and retrieval device 114 conventionally analyzes these data and generates the cross-sectional dimensions, preferably a model or image, of the scanned joint or tissue area at the location L, and this is fed to the display device 116 for viewing. Additionally, the nature and characteristics of the reflected ultrasound signal detected by the receiver sensor of the surface scanning element 118 and transmitted by the device for detecting swelling 104 to the archival storage and retrieval device 114 could be analyzed using a separate analyzer (not shown), such as a computer or a program, to determine the location and degree of inflammation via various properties, such as the particular echogenicity, of the reflected ultrasonic signal.

In another preferred embodiment of the present invention, as shown in FIGS. 1, 3, and 4, the device for detecting swelling 104 is a conventional magnetic resonance imaging (MRI) system. The sensing component 102 is a conventional magnetic resonance imaging coil and preferably is a restricted motion scanning element using a support structure 130 and a guide track structure 132 (FIG. 4). A conventional brace (not shown) may be used to hold the limb or other anatomic feature of the patient P being scanned. The magnetic resonance field is conventionally oriented and located in a reference spatial grid as with all conventional MRI devices. In operation, magnetically generated images or dimensions from the anatomy of the patient P at the location L are transmitted from the surface scanning element 118 to the device for detecting swelling 104 and this in turn is conventionally coupled to the archival storage and retrieval device 114. The archival storage and retrieval device 114 operates to conventionally analyze these MRI data and generate the cross-sectional dimensions, and preferably a model or image, of the area of the scanned joint or tissue at the location L. These analyzed data are then fed to the display device 116 for viewing. Additionally, the nature and characteristics of the returned MRI signal detected by the surface scanning element 118 can be analyzed by the archival storage and retrieval device 114 to determine the location and degree of inflammation via various properties of the MRI signal.

It should now be apparent to those skilled in the art that the imaging system 104 of the subject invention can be formed from various types of conventional dimensional measuring or imaging systems that are capable of producing detailed images and/or measurement of surfaces. Preferably, such systems should be such that they are easily adapted for use in developing detailed measurements, and preferably computerized models or images, of the joints or tissue. It should also now be apparent to those skilled in the art that other types of systems, such as wraps, cuffs, or sleeves having one or a plurality of location sensors may be used for placement about a joint or tissue area.

Figure 5:
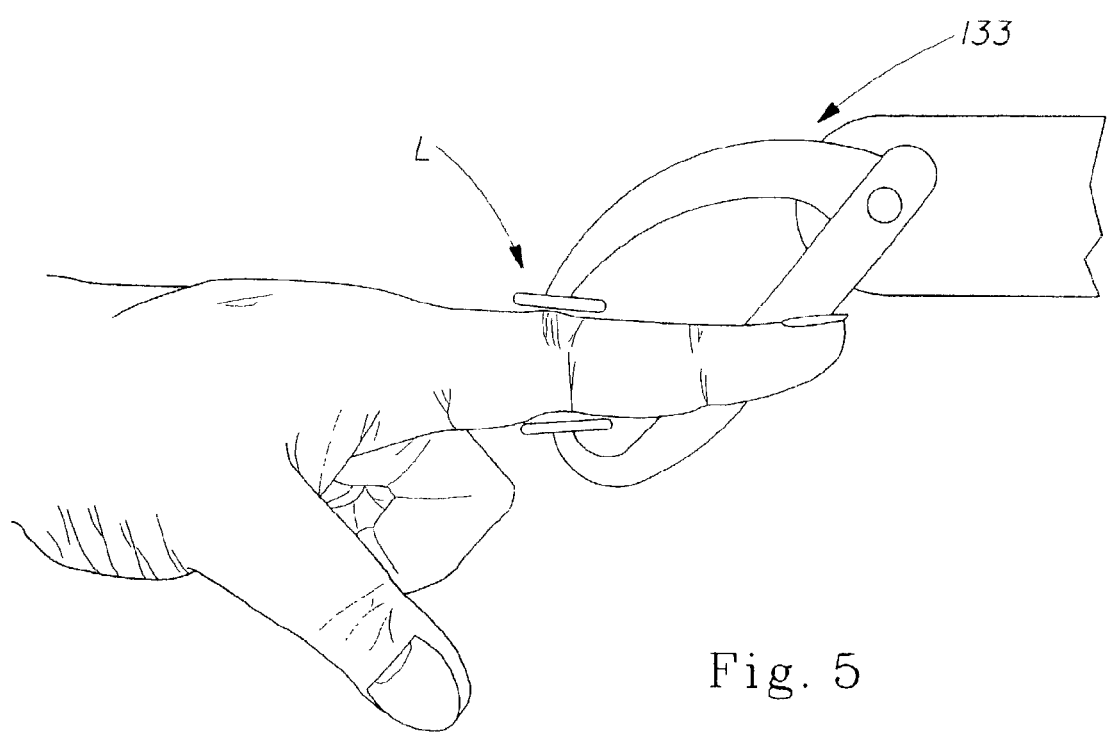
FIG. 5 is a schematic view of the imaging system of the apparatus for the detection and quantification of inflammation of FIG. 1 having mechanical calipers which are applied directly to the patient to measure the cross-sectional dimensions or elevations of the joint or tissue.

In another preferred embodiment of the invention, as shown in FIGS. 2 and 5, the imaging system 104 comprises mechanical calipers 133. In operation, the mechanical calipers 133 are applied to directly measure the cross-sectional dimensions or elevations of the joint or tissue at the location L. The position of the calipers 133 is determined by the position tracking system 126. The calibers 133 and the position tracking system 126 are coupled to the archival storage and retrieval device 114 for archival storage and retrieval and for correlating the data and generating the cross-sectional dimensions, and preferably a three-dimensional image of the joint or tissue at the location L.

It should now be apparent to those skilled in the art that the model(s) or image(s), if any, and the cross-sectional dimensions generated using the apparatus for the detection and quantification of joint and tissue inflammation 100 of the subject invention may be compared to a reference, such as a previously taken dimensional measurements and/or models or images of the location L, and slight variations in the position of the surface of the location L of the tissue or joint can be observed, thus allowing precise determination of any differences or changes of the subject joint or tissue cross-sectional area or dimensions.

Referring to FIGS. 1 and 2, the device for detecting swelling 104 preferably also operates as the range-of-motion device 106 of the present invention for determining the patient's range of motion of the joint being examined. Using the dimensional measurements and/or the images, if any, generated by the device for detecting swelling 104, the range-of-motion of the joint may be determined using the archival storage and retrieval device 114 to measure the changes in the position and deformation of certain preselected points within the location L being scanned as the joint is moved. The measurements can then be compared to a reference, such as a standard or the results of a previous scan, to determine any changes in the range of motion of the subject joint. While the range-of-motion device 106 preferably uses the images or measurements generated by the device for detecting swelling 104, it should now be apparent to those skilled in the art that other range-of-motion devices such as those using geometric charts and gages, optical grids, or those using mechanical systems known in the art for measuring ranges of motion may also be used and the results stored in the archival storage and retrieval device 114 for archival storage and retrieval and for correlating and analyzing the data and for generating a graphical illustration or measurement of the patient's range-of-motion. These data and the graphical illustrations can be fed into a display device 116 for viewing.

Figure 6:
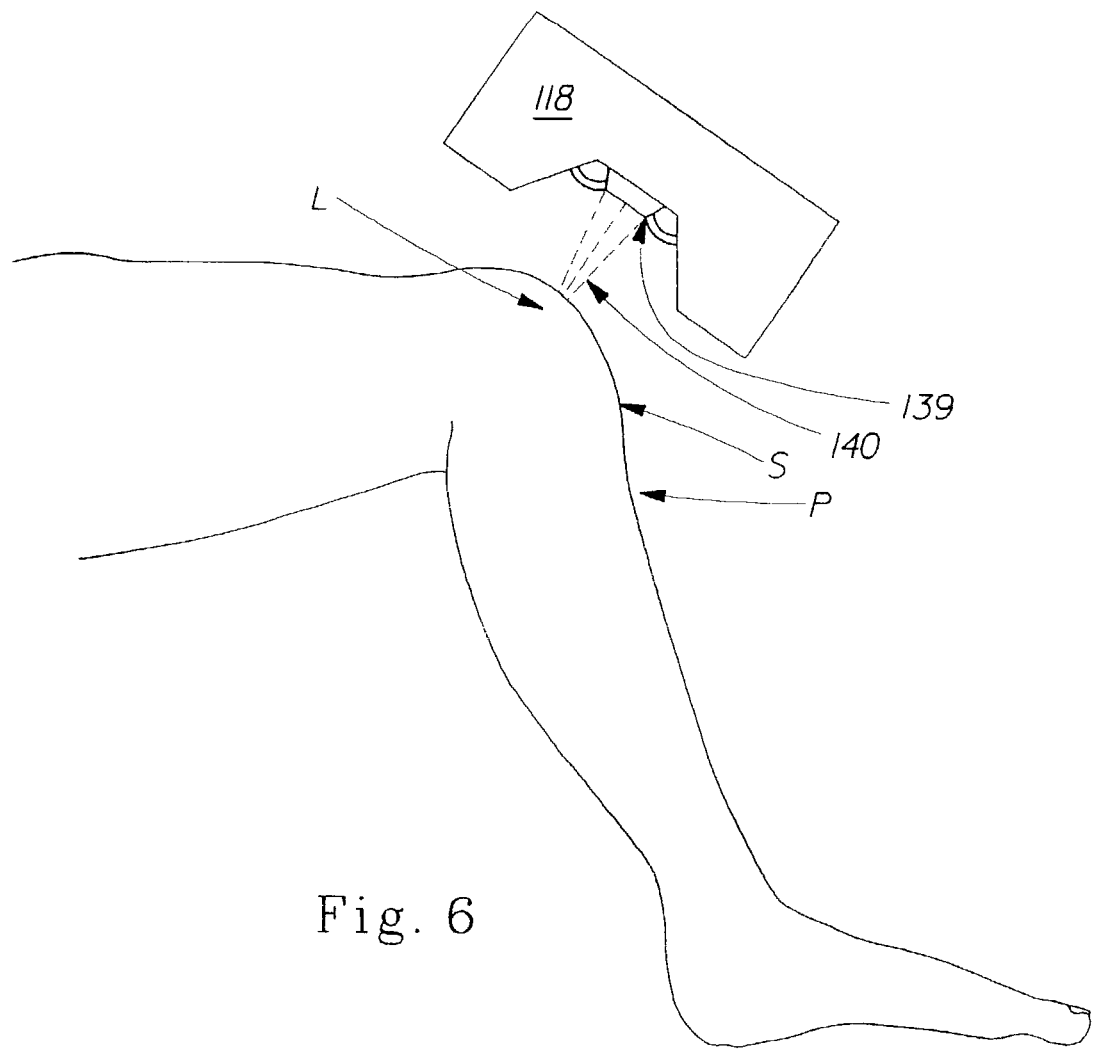
FIG. 6 is a schematic view of (he sensing component of the apparatus for the detection and quantification of inflammation of FIG. 1 showing the surface scanning element having a optical-, gloss-, or temperature-sensitive sensor.

The color analyzing device 108 for analyzing the color of the skin or tissue of the patient P at the location L of the tissue or joint being examined is shown in FIGS. 1 and 6. The color analyzing device 108 is coupled to the surface scanning element 118 of the sensing component 102, which preferably comprises a light-sensitive sensor for measuring color such as a colorimeter or a spectrophoto-meter. In operation, a patient P being tested for joint or tissue inflammation is arranged in such a manner that the tissue or joint to be examined is appropriately positioned for measurement by the apparatus of the present invention. The surface scanning element 118 is directed over the subject location L and the measurement of the wavelength and the intensity of the electromagnetic radiation being reflected from the location L is measured using the color analyzer of the color analyzing device 108. The color analyzing device 108 is coupled to the archival storage and retrieval device 114 for archival storage and retrieval and for comparing the data from the color analyzing system 108 to a standard or to a reference, such as previously taken measurements of the subject location L (or measurements of other noninflamed anatomical locations), for determining an increase or a decrease in inflammation. These data are then transmitted to the display device 116 for viewing.

In another preferred embodiment of the invention, the color analyzing device 108 is coupled to the surface scanning element 148 of the sensing component 102. Preferably, the surface scanning element 118 includes a light sensitive sensor, i.e. a glossmeter, for measuring the surface characteristics of the subject location L. In operation, photoelectric measurement of specularly reflected light from the surface of the skin S of the patient P at the location L is measured by the color analyzing device 108. The color analyzing, device 108 includes a gloss analyzer for comparing the collected data to a standard, a reference such as a previous measurements or the location L, or to measurements of other noninflamed anatomical locations, and is coupled to the archival storage and retrieval device 114 for archival storage and retrieval of the collected data and for comparing data from the color analyzing device 108 to a standard or to a reference, such as a previous taken measurements of the subject location L, or measurements of other noninflamed anatomical locations for determining an increase or decrease in inflammation. Additionally, the gloss reading from the surface scanning element 118 of the sensing component 102 could be fed to the device for detecting swelling 104 and then transmitted to the archival storage and retrieval device 114 which would analyze, or use an attached element or program (not shown) to analyze the gloss reading to determine the tissue stretch and thus the associated swelling of the joint or tissue at the location L of the patient P. These color or gloss data are then transmitted to the display device 116 for viewing.

Referring to FIGS. 1, 2, and 6, the temperature measuring device 110 for measuring the temperature in the location L of the tissue or joint to be examined is shown and is coupled to the sensing component 102 having a surface scanning element 118 for receiving temperature input of the subject location L. In a preferred embodiment of the invention, the surface scanning element 118 includes a light-sensitive sensor for receiving temperature input by measuring the intensity of an infrared light beam 140 which is reflected from the surface of the skin or tissue S of the patient P at the subject location L. Infrared sensing devices have been commercially available for measuring skin temperatures of patients. In a preferred embodiment of the invention, as shown, the surface scanning element 118 of the temperature measuring device 110 includes a conventional infrared sensor comprising an infrared detector 138 and a focusing element 139 for focusing incoming infrared radiation emitted from the skin or tissue S of the patient P onto the infrared detector or the surface scanning element 118. Broadcast radiation is detected by the surface scanning element 118 and the temperature is calculated using conventional circuitry within the temperature measuring device 110 that calculates subtle skin or tissue temperature variations. The temperature measuring device 110 correlates the data and compares the data to a standard or a reference, such as previous temperature measurements at that location L, and the difference in the intensity of the infrared light can be used to calculate the temperature and the change in temperature of the scanned location L. The temperature measuring device 110 is coupled to the archival storage and retrieval device 114 for calculating temperature changes and for archival storage and retrieval or the temperature data and for comparing the data to a standard or to a reference, such as previously taken measurements of the subject location L, for determining an increase or a decrease in inflammation. The archival storage and retrieval device 114 feeds the changes to the display unit 116 for viewing.

While preferably the surface scanning element 118 includes a light-sensitive sensor, other forms of sensors may also be utilized for measuring the skin or tissue S temperature of the patient P. In a preferred embodiment of the invention, the surface scanning element 118 comprises a conventional thermocouple temperature sensor whereby pairs of dissimilar metal alloy wires join at least one end, which generate a net thermoelectric voltage between the two ends according to the size of the temperature difference between the ends, the relative Seebeck coefficient of the wire pair and the uniformity of the wire's relative Seebeck coefficient.

In another preferred embodiment of the invention, the surface scanning element 118 comprises a conventional thermistor temperature sensor having electric contacts and lead conductors connected to the contact whereby the induced specific resistance across the thermistor is measured and converted to a specific temperature reading using conventional circuitry.

In another preferred embodiment of the invention, the surface scanning element 118 comprises a conventional resistance temperature detector whereby electrical current that produces a voltage drop across the sensor is measured and is converted to a temperature reading using conventional circuitry.

In another preferred embodiment of the invention, the surface scanning element 118 comprises a conventional pulsed laser beam temperature sensor whereby a first laser beam having a first wavelength is oscillated immediately after the rise of the pulsed laser beam, and a second laser beam having a second wavelength is oscillated thereafter. Based on the difference between the intensity of the first interfered light of reflected light of the first laser beam and the intensity of reflected light of the second laser beam, the temperature of the skin S of the patient P can be measured.

In another preferred embodiment of the invention, the surface scanning element 118 includes a conventional skin surface electrical conductance/resistance probe, similar to those in polygraph systems, comprising two electrodes which are placed in direct contact with the skin of the patient. In operation, the electrodes are provided with electric current that flows between them and changes in the conductance/resistance of the flow caused by insensible sweating at the location is measured. Since tissue temperature changes cause variations in insensible sweating and thus skin moisture, changes in skin electrical conductance/resistance occur and from these changes the temperature at the location of the probe can be derived using the archival storage and retrieval device 114.

It should now be apparent to those skilled in the art that the temperature measuring device 110 of the subject invention can be formed from various types of conventional temperature measuring devices that are capable of measuring the temperature of a surface. Such devices may include conventional medical thermography instrumentation, microwave thermography instrumentation for measuring natural radiation, infrared scanners, laser scanners, thermometers, resistance temperature detectors, thermistor temperature sensors, and thermocouple temperature sensors. Preferably, such devices should be easily adapted for use in developing detailed measurements of the temperature along the surface of the area of the joint or tissue being examined.

Figure 7:
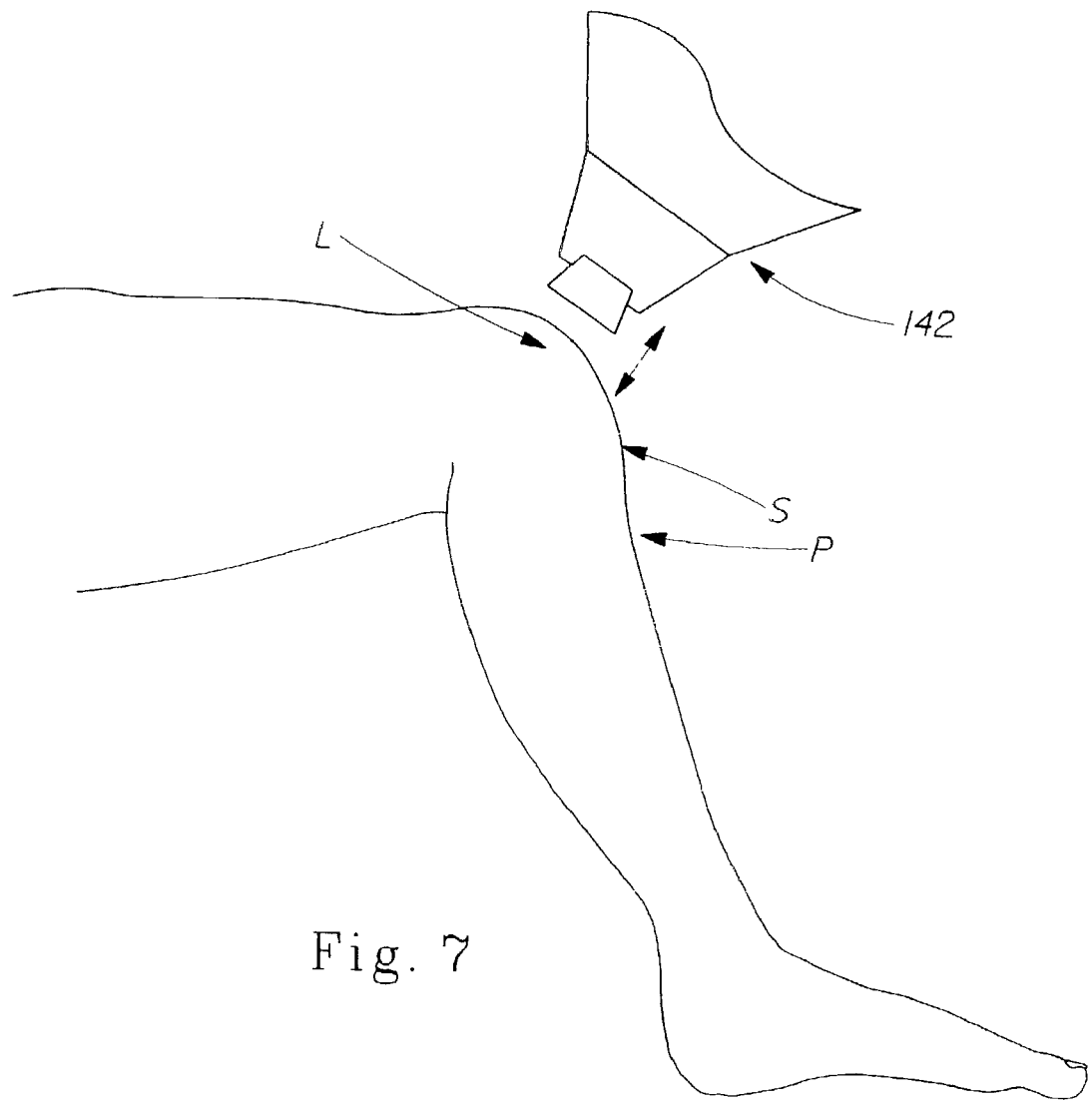
FIG. 7 is a schematic view of the sensing component of the apparatus for the detection and quantification of inflammation of FIG. 1, the sensing component having a probe for applying a stimuli to the patient at a location to determine pain tolerance and threshold.

Referring to FIGS. 1 and 7, the pain or tenderness detection device 112 for determining the presence of pain or tenderness is shown. In a preferred embodiment of the invention, the sensing component 102 includes a probe 142, such as a hand-held pressure probe, e.g a dolorimeter, to determine pain or tenderness threshold and tolerance of the patient P at the location L. In operation, the probe 142 comprises a pressing device, clamping device, sleeve, pinchers, or other like means for applying pressure against the skin S of the patient P at the location L being examined. Preferably, the pressure level necessary to produce pain or tenderness at the location L is sensed by the probe 142 via a button or other conventional triggering device (not shown) which the patient P activates when the applied pressure stimulus becomes painful, and this pressure level is then coupled to the to the archival storage and retrieval device 114 for converting the readings of the probe 142 into a graphical representation.

In another preferred embodiment of the invention, the sensing component 102 includes a probe 142 for producing a discrete area of heat. The probe 142 comprises a metal tip which is easily heated electrically. The heat level necessary to produce pain at the location L is determined via a button or other triggering device (not shown) which the patient P activates when the applied heat becomes painful, and this heal level is then fed to the pain detection device 112 which calculates the temperature at which the patient P experiences pain at the location L and this is transmitted to the an archival storage and retrieval device 114 for storage and retrieval of generated data and for analysis and is fed into the display 116 for viewing.

In another preferred embodiment of the invention, the sensing component 102 includes a probe 142, for producing discrete electrical stimuli. The probe 142 comprises a metal tip which is effective for electrically stimulating the tissue of the patient P at the location L. The electrical stimulus necessary to produce pain at the location L is determined via a button or other triggering device (not shown) which the patient P activates when the applied electrical stimulus becomes painful, and this stimulus level is then fed to the pain detection system 112 which then calculates the amount of electrical stimuli to determine the pain threshold and tolerance at the location L and this is transmitted to the archival storage and retrieval device 114 for archival storage and retrieval and for analysis and is fed into the display 116 for viewing.

It should now he apparent to those skilled in the art that pain and tenderness thresholds and tolerances will vary significantly between patients, and such quantified results together with visual observations will significantly improve reliability in assessing a patient's pain and tenderness thresholds and tolerances.

It should now be apparent to those skilled in the art that the present invention provides a novel non-human observer or non-clinician based apparatus and method for the detection and quantification of joint or tissue inflammation comprising an imaging or measuring system for obtaining data indicative of the surface and cross-sectional dimensions of the patient's tissue or skill, a color and/or gloss analyzing device for analyzing the color and/or gloss of the patient's tissue or skin, a temperature measuring device for measuring the temperature of the patient's tissue or skin, a pain detection device for determining the patient's threshold of tenderness or pain, and a device for determining the patient's range of motion at the location being examined. Accordingly, any two or more of the five cardinal signs or manifestations comprising redness, swelling, heat, pain, and the loss of function of the involved tissue, common to inflammation, can be recorded and analyzed by the examining physician, trainer, or health care worker. The presence of inflammation in the involved joint or tissue can be used as an indication of the presence of injury or disease, while the amount of inflammation in the injured, deformed, or arthritic joint or tissue can be used to determine the amount of damage or disease in that joint and whether the problem is progressing or healing.

It should be understood that the various groups of measurements of swelling, color, temperature, function or range-of-motion, and pain obtained using the apparatus for detecting and quantifying inflammation of a joint or tissue area of the subject invention will be used to detect and quantify the location and the amount of joint or tissue inflammation. It should now be apparent to those skilled in the art that mathematical algorithms or models may be developed to yield an overall inflammation quantity or score which can be used to assess the location and the degree of inflammation and any changes from baseline or previous measurements of inflammation.

It should now be apparent that the non-human observer or non-clinician based apparatus and method for the detection and quantification of joint and tissue inflammation of the subject invention eliminates observer subjectivity and inter-individual variation and thus providing better accuracy and reproducibility in the measurement of the detection and quantification of joint and tissue inflammation.

It should also now be apparent to those skilled in the art that the present invention provides a reliable and reproducible means whereby researchers can develop algorithms based on clinical studies that may be used to more accurately identify and quantify inflammation.

It should also now be apparent to those skilled in the art that the present invention provides a relatively inexpensive, reliable, reproducible, easy to use or perform, safe and noninvasive method and apparatus for the detection and quantification of joint and tissue inflammation that may be used in medical offices, clinics, training and sports facilities, and the like.

It should also nose be apparent to those skilled in the art that the method and apparatus for the detection and quantification of joint and tissue inflammation can also comprise operating instructions. Such instructions can be in the form of computer software stored within the computer, printed material attached to the apparatus or in the form of brochures or books. Although this invention has been shown and described with respect to detailed embodiments thereof, it will be understood by those skilled in the art that various changes in form and detail thereof may be made without departing from the spirit and scope of the claimed invention.

What is claimed is:

1. An apparatus for detecting and quantifying inflammation of a joint or tissue area comprising a sensing component; wherein said sensing component includes means for directly obtaining measurements of at least two of the cardinal signs of inflammation.

2. The Apparatus of claim 1 further comprising a device for storing the measurements and a display device for displaying the measurements.

3. The Apparatus of claim 1 further comprising means for comparing the measurements with previous measurements of the joint or tissue area.

4. The Apparatus of claim 1 wherein said sensing component comprises means for detecting swelling of the joint or tissue area.

5. The Apparatus of claim 4 wherein said means for detecting swelling is selected from the group consisting of mechanical contact devices, video-based digitizing scanning systems, optical scanning systems, laser-based systems, position tracking based system devices, glossmeter-based devices, ultrasound devices, and magnetic resonance imaging systems.

6. The Apparatus of claim 1 wherein said sensing component comprises a range-of-motion device determining the range of motion of the joint or tissue.

7. The Apparatus of claim 6 wherein said range-of-motion device is selected from the group consisting of geometric chart devices, geometric gage devices, optical grid devices, video-based digitizing scanning system devices, optical scanning system devices, laser-based system devices, position tracking based system devices, ultrasound-based devices, and magnetic resonance imaging and measuring system devices.

8. The Apparatus of claim 1 where said sensing component comprises a color analyzing device for analyzing the color of the area of the joint or tissue area.

9. The Apparatus of claim 8 wherein said color analyzing device is a light-sensitive sensor device.

10. The Apparatus of claim 8 wherein said color analyzing device is selected from the group consisting of colorimeters, spectrophotometers, and glossmeters.

11. The Apparatus of claim 1 wherein said sensing component comprises a temperature measuring device measuring the temperature of the joint or tissue area.

12. The Apparatus of claim 11 wherein said temperature measuring device is selected from the group consisting of mechanical contact devices, optical, laser-based, thermistor type, thermocouple-type, thermometer devices, thermography-type devices, infrared-based devices, light sensitive devices, and surface electrical conductance-resistance based devices.

13. The Apparatus of claim 1 wherein said sensing component comprises a pain or tenderness detection device determining the threshold and tolerance of pain or tenderness at the joint or tissue area.

14. The Apparatus of claim 13 wherein said pain or tenderness detection device Is selected from the group consisting of dolorimeter-type pressure devices, heating devices, and electrical stimuli devices.

15. The Apparatus of claim 1 further comprising means for generating an image of the joint or tissue area.

16. The Apparatus of claim 1 further comprising means for generating a mathematical model of the joint or tissue area.

17. The Apparatus of claim 1 further comprising means for analyzing collected measurements and generating an overall inflammation score.

18. A non-human observer based method of detecting and quantifying inflammation at a joint or tissue area comprising the steps of using an apparatus to obtain and collect data, the apparatus being capable of directly measuring at least two of the cardinal signs of inflammation, and analyzing said collected data to determine the presence of inflammation.

19. The method of claim 18 further comprising the step of storing the measurements and displaying the measurements for analyzing the amount and location of inflammation.

20. The method of claim 18 further comprising the step of comparing the measurements with previous measurements of the joint or tissue area.

21. The method of claim 18 wherein the apparatus comprises a device for detecting swelling of the joint or tissue area.

22. The method of claim 18 wherein the apparatus comprises a range-of-motion device for determining the range of motion of the joint or tissue.

23. The method of claim 18 where the apparatus comprises a color analyzing device for analyzing the color of the area of the joint or tissue area.

24. The method of claim 18 wherein the apparatus comprises a temperature measuring device for measuring the temperature of the joint or tissue area.

25. The method of claim 18 wherein the apparatus comprises a pain or tenderness detection device for determining the threshold and tolerance of pain or tenderness at the joint or tissue area.

26. The method of claim 18 further comprising a step of generating an image of the joint or tissue area.

27. The method of claim 18 further comprising a step of generating a mathematical model of the joint or tissue area.

28. The method of claim 18 further comprising a step of analyzing the collected measurements and generating an overall inflammation score.

29. A method for detecting and quantifying inflammation of a joint or tissue area comprising the steps of placing a patient in position for examination of the joint or tissue area; measuring two or more of the cardinal signs of inflammation at the joint or tissue area; automatically storing the measurements in an archival storage and retrieval device; deriving an inflammation score or quantity from the measurements and automatically comparing this inflammation score or the measurements against a baseline.

30. An apparatus for detecting and quantifying inflammation of a joint or tissue area comprising means for directly measuring the true physical measurements of the joint or tissue area, said measurements effective for detecting at least two of the cardinal signs of inflammation; and means for storing, retrieving, correlating and analyzing the data obtained.

31. The apparatus of claim 30 wherein said means for storing, retrieving, correlating and analyzing the data comprises a computer.

32. An apparatus for detecting and quantifying inflammation of a joint or tissue area comprising a sensing component having at least two different systems each system obtaining measurements of at least one of the cardinal signs of inflammation, wherein each system obtains measurements of a different cardinal sign of inflammation.

* * * * *